United States Patent [19]

Lindemans et al.

[11] Patent Number: 5,044,374
[45] Date of Patent: Sep. 3, 1991

[54] MEDICAL ELECTRICAL LEAD

[75] Inventors: Fred Lindemans, Limbricht, Netherlands; Clare Padgett, Minneapolis, Minn.; Thomas Kiekhafer, Coon Rapids, Minn.; Timothy Holleman, Ham Lake, Minn.; John Keimel, New Brighton, Minn.; David Peterson, Mounds View, Minn.

[73] Assignee: Medtronic, Inc., Minneapolis, Minn.

[21] Appl. No.: 376,730

[22] Filed: Jul. 7, 1989

Related U.S. Application Data

[63] Continuation-in-part of Ser. No. 264,916, Oct. 31, 1988, which is a continuation-in-part of Ser. No. 63,371, Jun. 18, 1987, Pat. No. 4,817,634.

[51] Int. Cl.⁵ ............................................. A61N 1/05
[52] U.S. Cl. .................................. 128/784; 128/419 D
[58] Field of Search ............... 128/419 D, 784–786, 128/798

[56] References Cited

U.S. PATENT DOCUMENTS

| | | | |
|---|---|---|---|
| 2,985,172 | 5/1961 | Jones | 128/784 |
| 4,282,886 | 8/1981 | King | 128/785 |
| 4,313,448 | 2/1982 | Stokes | 128/785 |
| 4,323,081 | 4/1982 | Wiebusch | 128/785 |
| 4,355,642 | 10/1982 | Alferness | 128/785 |
| 4,774,952 | 10/1988 | Smits | 128/419 D |
| 4,817,608 | 4/1989 | Shapland et al. | 128/419 P |

FOREIGN PATENT DOCUMENTS 2182566  5/1987  United Kingdom ............... 128/784

OTHER PUBLICATIONS

Adverse Effect of Permanent Cardiac Internal Defibrillator Patches on External Defibrillation, Joseph T. Walls. PACE, Jul.-Aug. 1987, Part II.

Primary Examiner—Ruth S. Smith

[57] ABSTRACT

A large surface electrode optimized for use as a subcutaneous defibrillation electrode. The electrode includes an insulative electrode pad carrying a large surface electrode. Both the upper and lower surfaces of the electrode pad are covered by a fabric mesh to reduce fluid build-up at the site of implantation. The defibrillation electrode is spaced at least 0.5" from the external periphery of the pad.

6 Claims, 1 Drawing Sheet

MEDICAL ELECTRICAL LEAD

This is a continuation-in-part of copending application U.S. Ser. No. 264916 filed on Oct. 31, 1988, which is a continuation-in-part of U.S. application Ser. No. 07/063,371, filed Jun. 18, 1987, now U.S. Pat. No. 4,817,634, issued Apr. 4, 1989.

BACKGROUND OF THE INVENTION

This invention relates to medical electrical stimulation electrodes in general and to subcutaneous defibrillation electrodes in particular.

In the past years, there has been a substantial activity directed toward development of a practical implantable defibrillator. Some approaches, such as those disclosed in U.S. Pat. No. 3,942,536 issued to Mirowski et al and U.S. Pat. No. 4,161,952 issued to Kinney et al have employed only endocardial electrodes. Alternate approaches to this problem have focused on systems employing one or more epicardial electrodes as alternatives to or in addition to endocardial electrodes. Some such systems are disclosed in U.S. Pat. No. 4,030,509 issued to Heilman et al and U.S. Pat. No. 4,291,707 issued to Heilman et al.

Use of epicardial electrodes has the disadvantage that it requires major surgery in order to mount the electrodes to the epicardium. Therefore, more recent approaches to the problem of an implantable defibrillator have employed a combination of endocardial and subcutaneous electrodes, rather than epicardial electrodes. One such system is disclosed in U.S. Pat. No. 4,727,877 issued to Kallok. Researchers have sometimes accomplished this change by simply implanting available epicardial electrodes subcutaneously.

SUMMARY OF THE INVENTION

One epicardial defibrillation electrode which is believed particularly adaptable to use as a subcutaneous electrode is illustrated in U.S. Pat. No. 4,817,634, issued to Holleman et al, Apr. 4, 1989, for an "EPICARDIAL PATCH ELECTRODE". This patent is incorporated herein by reference in its entirety. Additional improvements to this general electrode configuration are described in U.S. Patent Application Ser. No. 264,916 filed Oct. 31, 1988, for an "EPICARDIAL ELECTRODE LEAD", by Williams et al. This application is also incorporated herein by reference in its entirety.

The inventors of the present application have determined that in many cases, large surface area subcutaneous electrodes can lead to the production of excessive fluid build-up around the electrode. It is believed that the fluid build-up around the electrode may be caused by mechanical irritation of the tissue adjacent the electrode by the metal electrode surfaces. Subcutaneous electrodes according to the present invention employ a fabric mesh covering conductive surfaces of the electrode, and also optionally covering the insulated upper surface of the electrode.

Testing of the electrode described herein has shown a substantial reduction in the build-up of fluid around the electrode as compared to the electrode illustrated in FIG. 5 of the above-cited Holleman et al patent when used in subcutaneous implants.

BRIEF DESCRIPTION OF THE DRAWINGS

FIG. 1 shows a plan view of the lower surface of a defibrillation electrode according to the present invention. For purposes of this application, the lower surface is the surface bearing the conductive electrode surfaces. This electrode includes an insulative electrode pad 10 molded of silicone rubber. The pad is provided with a plurality of space wound coils 12A, 12B, 12C and 12D, embedded within corresponding elongated grooves 14A, 14B, 14C, and 14D, respectively. The construction of electrode pad 10, coils 12A-D and grooves 14A-D may correspond to that illustrated in FIG. 5 of the above-cited Holleman et al patent and FIG. 1 in the above-cited Williams et al application. As illustrated, coils 12C and 12D have twice the number of individual coil turns per unit of lineal length. This is intended to assist in reducing impedance along the exterior periphery of the electrode to avoid burning.

Figure 1:
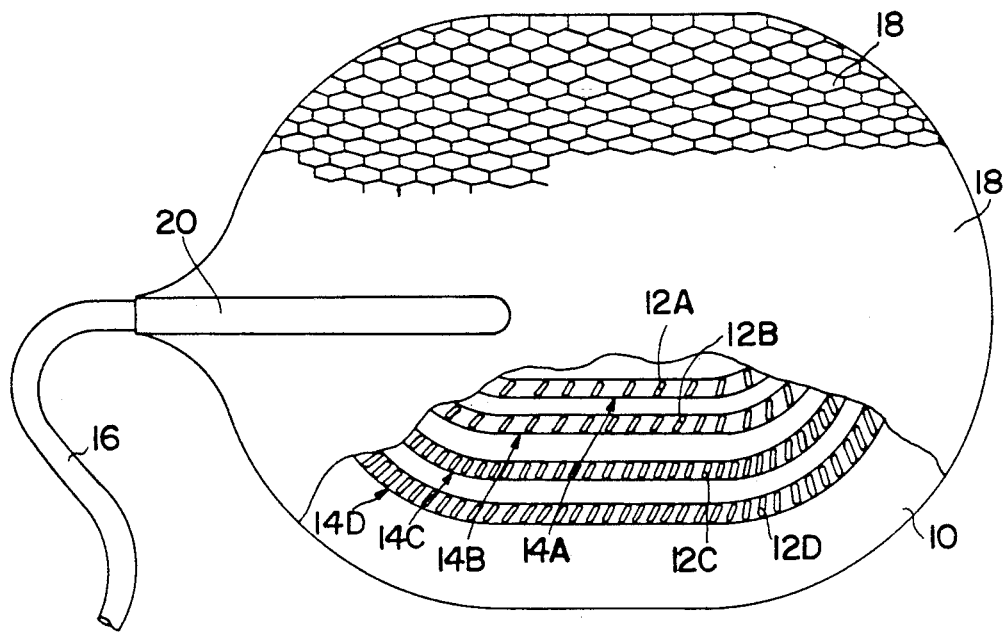
FIG. 1 is a bottom, cutaway view of an electrode according to the present invention.

It should be noted that in the embodiment illustrated in FIG. 1 of the present application, the electrode pad 10 extends a substantial distance beyond the periphery of outer conductor coil 12D. As implanted, the upper (insulated) surface of the lead will be facing outward. Provision of an electrode pad which extends substantially beyond the electrode coils is believed to reduce the chance that transthoracic defibrillation shocks applied in the vicinity of the electrode will propagate from the electrode to the defibrillator to which it is attached. In the embodiment illustrated, electrode pad 10 extends at least ¼" from the exterior periphery of electrode coil 12D.

The entire lower surface of electrode pad 10, including the electrode coils 12A-D, is covered by a Dacron mesh 18. Mesh 18 is adhesively bonded to base pad 10 around the periphery of the base pad and in the area 20 in which electrode coils 12A-D are coupled to insulated conductor 16. Conductor 16 serves to couple the electrode to the implantable defibrillator. The specific method for coupling conductor 16 to the individual coils 12A-D is illustrated in FIG. 6 of the above-cited Holleman et al patent.

Figure 2:
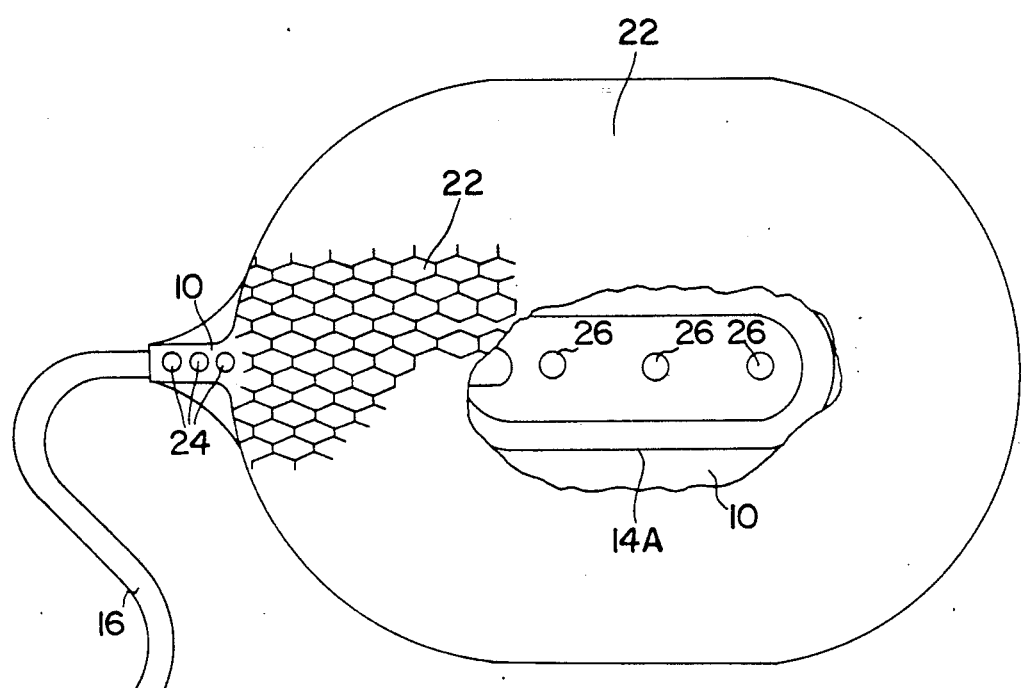
FIG. 2 is a top, cutaway view of an electrode according to the present invention.

FIG. 2 is a top, cutaway view of the electrode illustrated in FIG. 1. The entire upper surface of the electrode pad 10 is covered by a second layer of Dacron mesh 22, which is also adhesively attached to the electrode pad 10 around its external periphery only. The upper surface of electrode pad 10 at the point that conductor 16 departs from the pad is provided with three hemispherical bumps 24. These bumps are intended to indicate that this is the upper surface of the electrode, as the Dacron meshes 18 and 22 make both sides quite similar in appearance. In addition, in the preferred embodiment, three additional bumps 26 are molded on the center of the upper surface of the electrode pad 10, visible where mesh 22 is shown cut away. Bumps 26 are intended as tactile indicators of the upper surface of the pad and may easily be felt through mesh 22. An alternative method of marking would be to place a printed or woven marker into the mesh 22 itself.

While the invention is disclosed in the context of an electrode similar to those illustrated in the above-cited Holleman et al patent and Williams et al application, it is believed that the inclusion of Dacron meshes on the upper and lower surfaces of other versions of presently existing epicardial defibrillation electrodes such as those disclosed in the above-cited Heilman et al patents would also provide a substantial benefit. As such, the above description should be considered exemplary, rather than limiting with regard to the following claims.

In conjunction with the above specification, we claim:

1. An implantable defibrillation electrode apparatus comprising:
    an insulative electrode pad having upper and lower surfaces and having an outer periphery;
    a conductive electrode mounted to and exposed to the exterior of said electrode pad only along the lower surface of said electrode pad, said electrode extending no closer than 0.5" to the external periphery of said electrode pad.

2. A defibrillation electrode apparatus according to claim 1, wherein:
    said conductive electrode comprises an elongated electrode coil, exposed to the exterior of said electrode pad along the lower surface of said electrode pad.

3. A defibrillation electrode apparatus according to claim 2 wherein said electrode pad is provided with at least one elongated groove, in which said electrode coil is mounted.

4. A defibrillation electrode apparatus according to claim 3 wherein said electrode pad is provided with a plurality of grooves and wherein said conductive electrode comprises a plurality of elongated electrode coils, each of said elongated electrode coils located in one of said plurality of grooves provided in said electrode pad, and exposed to the exterior of said electrode pad along the lower surface of said electrode pad.

5. A defibrillation electrode apparatus according to claim 1 wherein the upper surface of said electrode pad is provided with means for indicating that said upper surface is the upper surface of said electrode pad.

6. A defibrillation electrode apparatus according to claim 1 further comprising a cloth mesh mounted to the lower side of said electrode pad and covering said conductive electrode, as viewed from the lower side of said electrode pad.

* * * * *